United States Patent
Puppo et al.

(10) Patent No.: US 6,261,752 B1
(45) Date of Patent: Jul. 17, 2001

(54) ALKALINE SOLUBLE MIXTURE COMPOSED OF CELLULOSE DERIVATIVES

(75) Inventors: Paola Puppo, Cogoleto; Alberto Valsecchi, Vado Ligure; Carlo Barlocco, Millesimo; Luisa Tavella, Bergeggi, all of (IT)

(73) Assignee: Ferrania S.p.A. (IT)

( * ) Notice: Subject to any disclaimer, the term of this patent is extended or adjusted under 35 U.S.C. 154(b) by 0 days.

(21) Appl. No.: 09/482,674

(22) Filed: Jan. 13, 2000

(30) Foreign Application Priority Data

Jan. 29, 1999 (IT) .................................. 99A000003

(51) Int. Cl.⁷ .............................. G03C 1/835; G03C 1/04
(52) U.S. Cl. ........................ 430/516; 430/531; 430/641
(58) Field of Search ................................. 430/516, 531, 430/639, 641

(56) References Cited

U.S. PATENT DOCUMENTS

| | | |
|---|---|---|
| 3,392,022 | 7/1968 | Gandy et al. . |
| 3,870,702 | 3/1975 | Koyanagi et al. . |
| 4,039,333 | 8/1977 | Shinagawa et al. . |
| 4,226,981 | 10/1980 | Onda et al. ........................... 430/516 |
| 4,262,088 | 4/1981 | Vallarino et al. .................... 430/514 |

FOREIGN PATENT DOCUMENTS 9738016   10/1997   (WO) .

*Primary Examiner*—Richard L. Schilling
(74) *Attorney, Agent, or Firm*—Mark A. Litman, Assoc.

(57) ABSTRACT

One object of the present invention is to provide a mixture composed of 1) a cellulose ether derivative esterified at least with a biprotic acid group derivative expressed by the formula HOOC—B—COOH (I), wherein B is a linear aliphatic group represented by $(CH_2)_x$ with x a positive integer from 1 to 5 or is a 5-member or 6-member cycloaliphatic group and 2) a cellulose or cellulose derivative esterified at least with a phthalic acid derivative represented by the following formula (II).

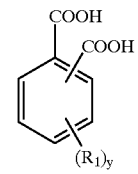

wherein $R_1$ is an all group and y is a positive integer from 0 to 3.

Said mixture shows an enhanced stability against hydrolysis when subjected to conditioning at high relative humidity and temperature.

The composition may be useful in order to get antihalation layer on photographic films as well as enteric coating of pharmaceutical dosage and for controlled-release applications such as for cleaning formulation.

7 Claims, No Drawings

ALKALINE SOLUBLE MIXTURE COMPOSED OF CELLULOSE DERIVATIVES

FIELD OF THE INVENTION

This invention relates to compositions of alkaline soluble cellulose derivatives which show an improved stability when subjected to conditioning at high relative humidity and temperature.

The cellulose derivatives composition of the invention is able to retain its property of being alkaline soluble after storage even in adverse conditions.

The composition may be useful in order to get antihalation layer on photographic films as well as enteric coating of pharmaceutical dosage and for controlled-release applications such as for cleaning formulation.

BACKGROUND OF THE ART

The problem of preventing halation in photographic elements is well known and various means have been designed to overcome this phenomenon. The photographic materials must be protected against the halation phenomenon which is caused by a light reflected from the base of the photographic material to the light sensitive layers. Said halation defect can be removed by coating a light-absorbing layer (generally called antihalo layer) on one of the surfaces of the support, usually the rear surface, so that rays which would otherwise be reflected onto the sensitive layer are thereby absorbed. Such antihalo layers generally consist of a dye or a pigment dispersed in a natural or synthetic binding resin.

There are basically two alternatives in the formulation of such antihalo layers: 1) the "decolorizable" type wherein dyes or the pigments included in the antihalo layer are decolorized during the processing, and 2) the "removable" type, wherein the binding resin is soluble during processing. In the removable type of antihalo layer binding resins, which must be soluble in the alkaine water solutions, and carbon black or colloidal carbon dispersed in such resin are used.

Colloidal carbon dispersions useful in antihalation backings have been described in U.S. Pat. No. 2,271,234 where an alkali soluble cellulose ester, in particular cellulose acetate phthalate, is used as binders for antihalation layers. Using a carrier of that type, as also described in U.S. Pat. No. 2,327,828, the antihalation layer is removable upon treatment in alkaline photographic developers. U.S. Pat. No. 3,392,022 discloses a photographic film support provided with a layer comprising a cellulose ester containing acetate radicals and radicals selected from the group consisting of hexahydrophthalyl and tetrahydrophthalyl and antihalation material.

In some recent development systems for black-and-white and color photography, the film is submerged in a preliminary imbibing (non-removing) bath, which is an alkaline solution of a high salt content. This solution makes the antihalo layer soluble (for example, a prebath or a backing removal solution); then after leaving the alkaline solution, the film is washed with water to remove the antihalo layer. It may be desirable furthermore to coat a magnetic track on the side of the support freed from said antihalo layer.

As a rule, the antihalo layer should not dissolve in such imbibing bath, which merely must salify the acid groups of the binding resin to give them the solubility in water. To prevent the contamination of the imbibing bath, the resin of the antihalo layer has to remain compact and must not dissolve in it, even if it is salified in said imbibing bath. Non-substantial removal of the antihalo layer in the imbibing bath is in fact necessary to avoid possible scratches on the film. During a following washing step with water, prior to entering the first developing bath, the antihalo layer must be easily and totally removed. Sometimes, in such washing step with water, jets of water under pressure are used to remove the whole layer perfectly.

It is very difficult to formulate antihalo layers which can be totally removed by means of mere water jets. If resins easily soluble in the alkaline water solutions are used to allow the total removal by means of mere water jets, the integrity of the anti-halo layer results to be too low to withstand the imbibing bath, such that it tends to contaminate the imbibing bath itself. If, on the contrary, a resin with a lower solubility in the alkaline water solution is used to have an integrity in the imbibing bath such as not to contaminate it, the removability of the antihalo layer by means of mere water jets is not totally assured and a thin veil of antihalo film may remain on the supporting base under the form of fog. Usually in the photographic process under consideration, after or during the washing steps with water jets, the photographic material dipped into current water is put in contact with rotating rollers covered with a soft material or with brushes provided with bristles, to remove the residual antihalo layer. Less than perfect functioning of the mechanical action of the rollers or brushes, due to wear or defects of the same, often causes an incomplete removal of the antihalo layer.

A material having an antihalo layer which retains its integrity in the imbibing bath and is easily removable in a subsequent washing step is described in U.S. Pat. No. 4,039,333; this layer includes a mixture of resin substantially consisting of a terpolymer containing from 10 to 25% of alkylacrylate units, from 52 to 65% of alkylmethacrylate units and from 18 to 30% acrylic or methacrylic acid, and a resin soluble in aqueous alkali solution. Such a layer, however, is not completely removable with water jets without the mechanical action exerted by the contact with the rotating rollers or brushes.

U.S. Pat. No. 4,262,088 describes a formulation for carbon black antihalation layer which comprises a mixture of two copolymers of low molecular weight alkylmethacrylate and acrylic or methacrylic acid. A resinous viscosity control agent soluble in alkaline solution, such as, for example, hydroxypropylmethyl cellulose phthalate, is also added to said composition.

Japanese Patent Application No. 61-094045 describes an antihalation layer which includes cellulose mixture ester having hexahydrophtharyl group or tetrahydrophtharyl group and hydroxyalkylalkyl cellulose acetate phthalate. Antihalation layer has improved humidity resistivity and is easily removable.

U.S. Pat. No. 3,870,702 discloses a coating composition consisting essentially of a solution of an organic solvent and at least one monoester selected from the group consisting of a tetrahydrophthalic acid monoester and hexahydrophthalic acid monoester of a cellulose ether.

U.S. Pat. No. 4,226,981 describes a method for preparing mixed ester selected from the class consisting of alkylcellulose, hydroxyalkylcellulose and hydroxyalkylalkyl cellulose esterified with acidic succinyl groups and acyl groups. The method for providing a halation preventing layer on the surface of a photographic film which comprises applying said solution of mixed esters is also described therein.

PCT application No. 97/38016 discloses a modified cellulose ester having formula: $\{(C_6H_7O_2)(OR)_x(OR')_y(OH)_{3-x-}$ $_y$} and characterized in that R is hydrophobic, R' is hydrophilic, relative to each other, but R' is not phthalyl or trimellityl and x, y and n are selected so that the modified cellulose ester will dissolve in aqueous solutions having a pH at or above 6.5, and not below.

Alkaline soluble cellulose derivatives are known to be used also as protective coatings on pharmaceutical solid dosage forms, particularly enterosoluble coatings. Properties generally required of enteric coating agents for medicament are insolubility in the stomach, solubility in the intestines and high moisture permeability resistance and stability. For such purpose, cellulose acetate phthalate has been widely employed, but they do not possess moisture permeability resistance and stability, so that during storage, it is liable to be hydrolized by the moisture contained in the air, thereby isolating acetic acid and greatly reducing the commercial value of the medicament. Other well known cellulose ethers and ether derivatives have not good enough solubilities in ordinary organic solvents, such as acetone, so that their coating methods are limited. Furthermore, they have poor moisture permeability resistance, which are apt to cause the medicaments treated with them to be degenerated while they are stored.

The cellulose derivatives described in the art do not have stability against hydrolysis when subjected to conditioning at high relative humidity and temperature.

SUMMARY OF THE INVENTION

One object of the present invention is to provide a mixture composed of 1) a cellulose ether derivative esterified at least with a biprotic acid group derivative expressed by the formula HOOC—B—COOH (I), wherein B is a linear aliphatic group represented by $(CH_2)_x$ with x a positive integer from 1 to 5 or is a 5-member or 6-member cycloaliphatic group and 2) a cellulose or a cellulose derivative esterified at least with a phthalic acid derivative represented by the following formula (II).

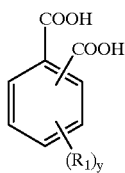

Formula (II)

wherein $R_1$ is an alkyl group and y is a positive integer from 0 to 3.

Said mixture shows an enhanced stability against hydrolysis when subjected to conditioning at high relative humidity and temperature.

Another object of the present invention is a photographic film which comprises a antihalo layer including said mixture as binder which allows the layer to be removed by a process that involves soaking the film in an alkaline solution, rinsing with water and scrubbing the backside layer, the antihhlo layer not being easily removable after the only action of being dipped in an allie solution, to prevent possible scratches on the film.

A third object of the present invention is to provide a solid dosage form with an enterosoluble coating layer characterized in that the coating layer comprises the mixture of above which do not dissolves in the gastric juice, but readily dissolves in the intestinal juice.

DETAILED DESCRIPTION OF THE INVENTION

The cellulose ether derivative is represented by the general formula (III) $(R^2_m R^3_n A)_p$, wherein $R_2$ is hydroxyalkyl group, $R^3$ is an alkyl group, A is a glucosic residue of the cellulose structure, m+n is 1 to 4 and p is an integer lower than 5,000.

Preferably, in the above formula (III), $R^2$ is a hydroxyalkyl group, such as hydroxyethyl, hydroxypropyl or hydroxybutyl, $R^3$ is an alkyl group, such as methyl, ethyl, propyl or butyl; more preferably, m is 1, n is 1 and p is an integer lower than 2,000.

Illustrative examples of the above-defined cellulose ether derivatives are alkylcellulose, such as methylcellulose, ethylcellulose and propylcellulose; hydroxyalkyl celluloses, such as hydroxyethyl cellulose, hydroxypropyl cellulose and hydroxybutyl cellulose; hydroxyalkylalkyl celluloses, such as hydroxyethylmethyl cellulose, hydroxymethylethyl cellulose, hydroxypropylmethyl cellulose, hydroxypropylethyl cellulose, hydroxybutyl-methyl cellulose, hydroxybutylethyl cellulose; and those having two or more hydroxyalkyl groups, such as hydroxyethylhydroxypropylmethyl cellulose.

The cellulose ether derivatives of above are esterified with substituted or not substituted biprotic acid groups represented by the formula (I) of above, having a free carboxyl group allowing the cellulose derivatives to be soluble in alkline solutions, besides possessing high solubility in organic solvents and excellent resistance to water. Suitable aliphatic biprotic acid groups are, for example, malonic acid, succinic acid, glutaric acid, adipic acid, each of them can be substituted for example with alkyl groups having from 1 to 4 carbon atoms, such as methyl, ethyl, propyl and the like. Suitable 5-member or 6-member cycloaliphatic groups are, for example, hexahydrophthalyl groups and tetrahydrophthalyl groups, each of them can be substituted for example with alkyl groups having from 1 to 4 carbon atoms, such as methyl, ethyl, propyl and the like.

The cellulose ether derivatives of above, esterified at least with a biprotic acid group derivative, can be optionally esterified also with acyl groups, represented by the general formula R—CO—, where R is an aliphatic monovalent hydrocarbon group. Useful acyl groups used to esterify the cellulose ethers of above, are for example, the acetyl groups.

Suitable compounds obtained by esterification of cellulose ether derivatives with biprotic acid groups represented by the formula (I) of above are, for example, hydroxyethylmethylcellulose acetate succinate, hydroxymethylethyl cellulose succinate, hydroxypropylmethyl cellulose acetate succinate, hydroxypropylmethyl cellulose acetate glutarate, hydroxybutylmethyl cellulose acetate succinate, and the like.

The phthalic acid derivatives represented by the formula (II) of above are selected from the group of phthalic acid, isophthalic acid, terephthalic acid, being optionally substituted on the aromatic ring with alkyl groups having from 1 to 4 carbon atoms, such as methyl, ethyl, propyl and the like.

Suitable examples of cellulose or cellulose derivatives esterified with phthalic acid derivatives represented by the formula (II) of above are cellulose, carboxyalkyl cellulose, such as carboxymethyl cellulose, carboxyethyl cellulose, sodium carboxymethylcellulose, cellulose ethers, such as, for example, the cellulose ether derivatives described above, microcrystalline cellulose and cellulose sulfates. Preferred examples are the cellulose ether derivatives, such as alkylcellulose, hydroxy alkylcellulose and hydroxyalkylalkyl celluloses, as described above.

The cellulose or cellulose ether derivatives esterified with phthalic acid derivatives represented by the formula (II) of above, can be optionally esterified also with acyl groups, represented by the general formula R—CO—, where R is an aliphatic monovalent hydrocarbon group. Useful acyl groups used to esterify the cellulose or cellulose derivatives of above, are for example, the acetyl groups.

Suitable compounds obtained by esterification of cellulose or cellulose derivatives with phthalic acid derivatives represented by the formula (II) of above are, for example, hydroxyethylmethyl cellulose phthalate, hydroxymethylethyl cellulose phthalate, hydroxypropylmethyl cellulose phthalate, hydroxybutylmethyl cellulose phthalate, and the like.

The cellulose derivatives and cellulose ether derivatives are not limitative in molecular weight and in the degree of substitution with the hydroxyalkoxy and/or alkyl groups thereof. It is preferred that, in an alkylcellulose or a hydroxyalkylcellulose, the number of the substitutions of the hydroxy groups per glucose unit of the cellulose derivative does not exceed 2.5 on average, since a larger content of the substitutions brings about some difficulties in the preparation. It is also preferred that the value of p in the formula (III) of above is lower than 5,000, more preferably lower than 2,000.

The two alkaline soluble esters that form the mixture of the present invention can be added in suitable amounts to allow the mixture to be stable against hydrolysis when subjected to conditioning at high relative humidity and temperature. The ratio between the amount in weight of cellulose ether derivative esterified with aliphatic biprotic acid groups represented by the formula (I) and the amount in weight of the cellulose or cellulose derivatives esterified with phthalic acid derivatives represented by formula (II) is from 1:1 to 25:1, preferably from 3:1 to 15:1.

The present invention further consists of a photographic material comprising a support base, at least one silver halide emulsion layer coated on one side of said support base and an antihalo layer coated on the other side of said support base, such antihalo layer substantially consisting of an antihalo agent and of the alkali soluble mixture of the present invention described above.

The preferred antihalo agent is carbon black, i.e. finely grinded carbon formed by particles having a diameter ranging from 1 to 100 $\mu$. Many types of finely grinded carbons are known, but the best ones are those which can be easily dispersed together with the soluble mixture composed of cellulose derivatives of the present invention, e.g. Vulcan™ XC-72 (produced by Cabot Corporation) which is furthermore highly conductive. Dispersed colloidal carbons or antihalo dyes can also be used.

Many types of dispersing agents can also be used to disperse carbon black and give stable dispersions; those most well known are the polynaphthalenesulfonates.

Many useful solvent combinations have been found to form the alkline soluble mixture composed of cellulose derivatives of the present invention. As known in the art, these solvent combinations can be chosen according to the particular supporting base on which the antihalo composition is to be coated. Useful solvents may be, for example, methanol, acetone, methylcellosolve, ethylenglycole, and the like.

The antihalo composition in accordance with the present invention can be coated on the hydrophobic supporting base of the photographic material by following various known techniques, such as for instance, the spray, brush, roller, doctor blade, air knife technique, etc.

The antihalo layers in accordance with the present invention are provided on various suitable supports, such as cellulose esters supports (e.g., cellulose triacetate supports), paper supports, polyesters film supports (e.g., polyethylene terephthalate or PET film supports and polyethylene naphthalate or PEN film supports), and the like, as described in Research Disclosure 308119, Section XVII, 1989, thus obtaining a swell a fairly good adherence of the antihalo layer. The supports may be provided with a subbing layer, if necessary.

The opposite supporting base side is provided with at least a silver halide emulsion layer. Suitable silver halide emulsions can be any of the silver halide emulsions known in the art such as silver chloride, silver bromide, silver bromochloride, silver chloro-iodide, silver bromo-iodide, silver chloro-bromo-iodide emulsions and mixtures thereof. The emulsions can be composed of coarse, medium and fine grains and can be monodispersed or polydispersed. The silver halide grains may be those having a regular crystal form, such as a cube or an octahedron, or those having an irregular crystal form, such as spherical or tabular, etc., or may be those having a composite crystal form. They may be composed of a mixture of grains having different crystal forms. Their size can be varied on a wide range, but in general average grain sizes from 0.1 to 4 $\mu$m are suitable.

The silver halide emulsions may be obtained according to any of the known acid, neutral and ammoniacal method using conventional precipitation methods such as a single or twin jet method. Further, the silver halide emulsions may be chemically sensitized with a sulfur sensitizer, such as allylthiocarbamide, thiourea, cystine, etc.; an active or inert selenium sensitizer; a reducing sensitizer such as stannous salt, a polyamine, etc.; a noble metal sensitizer, such as gold sensitizer, more specifically potassium aurithiocyanate, potassium chloroaurate, etc.; or a sensitizer of a water soluble salt such as for instance of ruthenium, rhodium, iridium and the like, more specifically, ammonium chloropalladate, potassium chloroplatinate and sodium chloropalladite, etc.; each being employed either alone or in a suitable combination.

Furthermore, the above silver halide emulsions may contain various known additives for photography. For example, there may be employed additives for photography as disclosed in Research Disclosure, Item 17643, December 1978. Specifically hydrophobic photographic additives include dye-forming couplers, development-in-hibitor-releasing (DIR) couplers, silver halide developers, oxidized developer scavengers, spectral sensitizers and desensitizers, diffusion transfer dye image-formers, visible and ultraviolet light absorbers, which are conventionally introduced in hydrophilic colloid layers of photographic elements dispersed in water-immiscible high boiling solvents. Other hydrophobic photographic additives include those used in silver halide photographic elements such as optical brighteners, antioxidants, silver halide solvents, bleachable dyes and the like. Hydrophobic photographic additives for use in the present invention are described in more details in Research Disclosure 15930, July 1977.

Moreover, the silver halides may be optically sensitized to a desired region of the visible spectrum. The method for spectral sensitization is not particularly limited. For example, optical sensitization may be possible by using an optical sensitizer, including a cyanine dye, a merocyanine dye, complex cyanine and merocyanine dyes, oxonol dyes, hemioxonol dyes, styryl dyes and streptocyanine dyes, either alone or in combination. Particularly useful optical sensitizers are the dyes of the benzoxazole-, benzimidazole- and benzothiazole-carbocyanine type.

The above emulsions may also contain various additives conveniently used depending upon their purpose. These additives include, for example, stabilizers or antifoggants such as azaindenes; triazoles, tetrazoles, imidazolium salts, polyhydroxy compounds and others; film hardeners such as of the aldehyde, aziridine, isoxazole, vinylsulfone, acryloyl, triazine type, etc.; developing promoters such as benzyl alcohol, polyoxyethylene type compounds, etc.; image stabilizers such as compounds of the chromane, cumarane, bisphenol type, etc.; and lubricants such as wax, higher fatty acids glycerides, higher alcohol esters of higher fatty acids, etc. Also, coating aids, modifiers of the permeability in the processing liquids, defoaming agents, antistatic agents and matting agents may be used. As hydrophilic colloids to be used in the emulsion according to the present invention, not only gelatin but also gelatin derivatives, polymer grafts of gelatin, synthetic hydrophilic macromolecular substances and natural hydrophilic macromolecular substances other than gelatin may also be available either singly or in a mixture. Also, synthetic latexes may be added to gelatin to improve the film properties such as copolymers of acrylic acid esters, vinyl esters, etc. with other monomers having ethylenic groups.

The photographic emulsions can be used for black-and-white light-sensitive negative elements, light-sensitive positive elements, X-Ray elements, lithographic elements, black-and-white and color light-sensitive elements for diffusion transfer processes and light-sensitive elements which contain oil-soluble or water-soluble color couplers.

Preferably, the silver halide emulsions are designed for multicolor elements comprising dye image forming units sensitive to each of the three primary regions (blue, green and red) of the visible spectrum. Each unit can be formed by a single emulsion layer or multiple emulsion layers sensitive to the same spectral region.

More preferably, the silver halide emulsions are designed for a multicolor element comprising a support bearing at least one blue-sensitive silver halide emulsion layer and preferably two blue-sensitive silver halide emulsion layers of different sensitivity associated to yellow dye forming couplers, at least one green sensitive silver halide emulsion layer and preferably at least two green-sensitive silver halide emulsion layers of different sensitivity associated to magenta dye forming couplers, at least one red-sensitive silver halide emulsion layer and preferably at least two red-sensitive silver halide emulsion layers of different sensitivity associated to cyan dye forming couplers, and additional non light-sensitive hydrophilic colloid layers (such as protective layers, intermediate layers, filter layers, subbing layers, backing layers and the like), wherein at least one component layer of said material comprises incorporated therein a hydrophilic photographic additive dispersed with the aid of a water-immiscible high boiling organic solvent according to the present invention, said component layers comprising preferably at least one silver halide emulsion layer including a dye forming coupler.

The photographic elements can be processed after exposure to form a visible image. Processing can be the common processing employed to develop color photographic elements. A negative colored image can be obtained by color development followed by bleaching and fixing. Development is obtained by contacting the exposed silver halides of the element with an alkaline aqueous medium in the presence of an aromatic primary amine color developing agent contained in the medium or in the material, as known in the art. The aromatic primary amine color developing agent used in the photographic color developing composition can be any of known compounds of the class of p-phenylendiamine derivatives, widely employed in various color photographic process. Particularly useful color developing agents are the p-phenylenediamine derivatives, especially the N,N-dialkyl-p-phenylenediamine derivatives wherein the alkyl groups or the aromatic nucleus can be substituted or not substituted.

Examples of p-phenylenediamine developers include the salts of: N,N-diethyl-p-phenylenediamine, 2-amino-5-diethylamino-toluene, 4-amino-N-ethyl-N-($\alpha$-methanesulphonamidoethyl)-m-toluidine, 4-amino-3-methyl-N-ethyl-N-($\alpha$-hydroxyethyl)-aniline, 4-amino-3-($\alpha$-methylsulfonamidoethyl)-N,N-diethylaniline, 4-amino-N,N-diethyl-3-(N'-methyl-$\alpha$-methylsulfonamido)-aniline, N-ethyl-N-methoxy-ethyl-3-methyl-p-phenylenediamine and the like, as described, for instance, in U.S. Pat. Nos. 2,552,241; 2,556,271; 3,656,950 and 3,658,525.

Examples of commonly used developing agents of the p-phenylene diamine salt type are: 2-amino-5-diethylaminotoluene hydrochloride (generally known as CD2 and used in the developing solutions for color positive photographic material), 4-amino-N-ethyl-N-($\alpha$-methanesulfonamidoethyl)-m-toluidine sesquisulfate monohydrate (generally known as CD3 and used in the developing solution for photographic papers and color reversal materials) and 4-amino-3-methyl-N-ethyl-N-($\beta$-hydroxyethyl)-aniline sulfate (generally known as CD4 and used in the developing solutions for color negative photographic materials).

The color developing agents are generally used in a quantity from about 0.001 to about 0.1 moles per liter, preferably from about 0.0045 to about 0.04 moles per liter of photographic color developing compositions.

In the case of color photographic materials, the processing comprises at least a color developing bath and, optionally, a prehardening bath, a neutralizing bath, a first (black and white) developing bath, etc. These baths are well known in the art and are described for instance in Research Disclosure 17643, 1978, and in Research Disclosure 308119, Sections XIX and XX, 1989.

After color development, the image-wise developed metallic silver and the remaining silver salts generally must be removed from the photographic element. This is performed in separate bleaching and fixing baths or in a single bath, called blix, which bleaches and fixes the image in a single step. The bleaching bath is a water solution having a pH equal to 5.60 and containing an oxidizing agent, normally a complex salt of an alkali metal or of ammonium and of trivalent iron with an organic acid, e.g., $EDTA.Fe.NH_4$, wherein EDTA is the ethylenediamino-tetracetic acid, or $PDTA.Fe.NH_4$, wherein PDTA is the propylenediaminotetraacetic acid. While processing, this bath is continuously aired to oxidize the divalent iron which forms while bleaching the silver image and regenerated, as known in the art, to maintain the bleach effectiveness. The bad working of these operations may cause the drawback of the loss of cyan density of the dyes.

Further to the above mentioned oxidizing agents, the blix bath can contain known fixing agents, such as for example ammonium or alkali metal thiosulfates. Both bleaching and fixing baths can contain other additives, e.g., polyalkyleneoxide compounds, as described for example in GB patent 933,008 in order to increase the effectiveness of the bath, or thioether compounds known as bleach accelerators.

The present invention further consists of a pharmaceutical solid dosage forms to be coated with the mixture of cellulose derivatives of the present invention include tablets, pills, granules, beads, capsules and the like, and the coating is performed by use of a conventional coating machine, such as pan coater, drum-type coating machine, or fluidization coating machine, with no specific limitation in operational conditions. As the coated medicament leaves the stomach and enters the small intestine, the pH increases to above about 5, whereupon the pendant carboxyl groups begin to ionize, and the coating begins to dissolve, releasing the medicaments The invention is now further illustrated with more details in the following examples.

EXAMPLES

Dispersion A was prepared to contain 11 gr. of carbon black Vulcan™ XC-72 (produced by Cabot Corporation), 1.1 g of disodium salt of methylene dinaphthalene sulphonic acid, 50 ml of propylene glycol methyl ether (commercially available from Dow Chem as Dowanol™ PM), 70 ml of methanol and 70 ml of distilled water and then milled in a bead mill for 4 hours (glass beads diameter=2 mm). In the meanwhile, Dispersions 1–6 were prepared according to Table 1 and then added to Dispersion A and milled for additional 4 hours.

TABLE 1

|  | Disp. 1 (Comp.) | Disp. 2 (Comp.) | Disp. 3 (Comp.) | Disp. 4 (Comp.) | Disp. 5 (Comp.) | Disp. 6 (Inv.) |
| --- | --- | --- | --- | --- | --- | --- |
| CAHP (gr) |  |  |  | 27, 5 | 25, 5 |  |
| ASH-G (gr) |  |  | 27, 5 |  |  | 25, 5 |
| HP50 (gr) | 27, 5 |  |  |  | 2, 0 | 2, 0 |
| HP55 (gr) |  | 27, 5 |  |  |  |  |
| Acetone (ml) | 310 | 310 | 310 | 310 | 310 | 310 |
| Methanol (ml) | 460 | 460 | 460 | 460 | 460 | 460 |
| Dowanol ™ PM (ml) | 40 | 40 | 40 | 40 | 40 | 40 |

Description of the ingredients of the formulations:
1) HP50, HP55: different molecular weight hydroxypropyl methylcellulose phthalate (HPMCP) commercially available from Shin Etsu Chemical Co.
2) ASH-G: hydroxypropyl methyl cellulose acetate succinate (HPMCAS), commercially available from Shin Etsu Chemicals Co.
3) Cellulose acetate hexahydrophthalate (CAHP): synthesized according to the method described in the art (FR 1,393,927); hexahydrophthalyl percentage=28

Samples 1–6 have been obtained by adding, respectively, dispersions 1–6 to dispersion A, and then by coating them on a cellulose triacetate film support by double rolls coating system at a wet coverage of 30–35 ml/m2. The samples have been dried at T=60° C. for about 2 minutes and at T=90° C. for additional 3 minutes. Part of the Samples 1–6 has been not submitted to conditioning test, while another part of Samples 1–6 has been tested by conditioning the film at a temperature of 23° C., 85% of relative humidity for one day and then sealed in an envelope and kept at a temperature of 50° C. for seven days.

Samples 1–6 not conditioned and Samples 1–6 conditioned according to the test of above have been put in an alkaline pre-bath at room temperature for 10 seconds. The alkaline pre-bath consisted in 20 gr. of borax decahydrated, 100 gr. of sodium sulfate anhydrous, 1 gr. of sodium hydroxide and water to make 1 liter. After the immersion of samples 1–6 in said pre-bath and the mechanical action of a brush, the removal of the antihalo layer has been verified. Then, the same check has been done on the samples that, immediately after the immersion for 10 seconds in the pre-bath, have been put under a jet of water for a few seconds, the residual antihalo being removed with the mechanical action of a brush. The results are shown in Table 2, where "yes" indicates the removal of the antihalo layer and "no" the not-removal.

TABLE 2

|  | After pre-bath only No test conditioned | After pre-bath and water jet No test conditioned | After pre-bath only Test conditioned | After pre-bath and water jet Test conditioned |
| --- | --- | --- | --- | --- |
| Sample 1 (Comp.) | yes | — | — | — |
| Sample 2 (Comp.) | yes | — | — | — |
| Sample 3 (Comp.) | no | yes | no | no |
| Sample 4 (Comp.) | no | yes | no | no |
| Sample 5 (Comp.) | no | yes | no | no |
| Sample 6 (Inv.) | no | yes | no | yes |

Table 2 shows that comparison Samples 1 and 2, containing a dispersion including hydroxypropyl methylcellulose phthalate compound only, without being submitted to conditioning test, are not acceptable because after the immersion in the prebath the antihalo layer is easily removed. Comparison Sample 3, containing a dispersion including hydroxypropyl methylcellulose acetate succinate compound only, and comparison Sample 4, containing a dispersion including cellulose acetate hexahydrophthalate compound only, are not acceptable because, after conditioning, some residual of antihalo layer were left even after the water jet action and the mechanical action of a brush. For the same reason, Sample 5, containing a dispersion including the combination of cellulose acetate hexahydrophthalate compound with including hydroxypropyl methylcellulose phthalate compound, is also not acceptable. On the contrary, Sample 6 of the present invention, which combines hydroxypropyl methylcellulose phthalate with hydroxypropyl methylcellulose acetate succinate, shows that the antihalo layer is removed only after water jet action, the residual antihalo being removed with the mechanical action of a brush. As described in prior art (see U.S. Pat. No. 4,262,088) the antihalation layer should not dissolve in the pre-bath, which merely must salify the acid groups of the binding resins to give them solubility in water. To prevent the contamination of the imbibing bath, the resin of the antihalo layer has to remain compact and must not dissolve in it, even if it is salified in said pre-bath. Non substantial removal of the antihalo layer in the imbibing bath is in fact necessary to avoid possible scratches on the film.

What is claimed is:

1. A photographic film provided with an antihalo layer on one of its surface which comprises a mixture composed of 1) a cellulose ether derivative esterified at least with a biprotic acid group derivative expressed by the formula HOOC—B—COOH (I), wherein B is a linear aliphatic group represented by $(CH_2)_x$ with x a positive integer from 1 to 5 or is a 5-member or 6-member cycloaliphatic group and 2) a cellulose or cellulose derivative esterified at least with a phthalic acid derivative represented by the following formula (II):

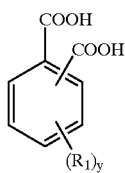

Formula (II)

wherein $R_1$ is an alkyl group and y is a positive integer from 0 to 3.

2. A photographic film as in claim 1, wherein the cellulose ether derivative is represented by the general formula $(R^2_m R^3_n A)_p$, wherein $R^2$ is hydroxyalkyl group, $R^3$ is an alkyl group, A is a glucosic residue of the cellulose structure, m+n is 1 to 4 and p is an integer lower than 5,000.

3. A photographic film as in claim 1, wherein the cellulose ether derivatives are selected from the group consisting of alkylcelluloses, hydroxyalkylcelluloses, hydroxyalkylalkylcelluloses.

4. A photographic film as in claim 1, wherein the cellulose ether derivatives esterified at least with a biprotic acid group derivative are also esterified with acyl groups.

5. A photographic film as in claim 1, wherein the cellulose ether derivatives esterified at least with a biprotic acid group derivative are selected from the group consisting of hydroxyethylmethyl cellulose acetate succinate, hydroxymethylethyl cellulose succinate, hydroxypropylmethyl cellulose acetate succinate, hydroxypropylmethyl cellulose acetate glutarate, and hydroxybutylmethyl cellulose acetate succinate.

6. A photographic film as in claim 1, wherein the cellulose or cellulose derivatives esterified with at least a phthalic acid derivative are selected from the group consisting of hydroxyethylmethyl cellulose phthalate, hydroxymethylethyl cellulose phthalate, hydroxypropylmethyl cellulose phthalate, and hydroxybutylmethyl cellulose phthalate.

7. A photographic film as in claim 1, wherein the ratio between the amount in weight of cellulose ether derivative esterified with aliphatic biprotic acid groups represented by the formula (I) and the amount in weight of the cellulose or cellulose derivatives esterified with phthalic acid derivatives represented by formula (II) is from 4:1 to 20:1.

* * * * *